United States Patent [19]

Maxwell et al.

[11] Patent Number: 4,951,669

[45] Date of Patent: Aug. 28, 1990

[54] BLOOD PARAMETER MEASUREMENT SYSTEM

[75] Inventors: Thomas P. Maxwell, Santa Ana; Thomas G. Hacker, Anaheim, both of Calif.

[73] Assignee: Minnesota Mining and Manufacturing Company, St. Paul, Minn.

[21] Appl. No.: 229,703

[22] Filed: Aug. 8, 1988

Related U.S. Application Data

[63] Continuation-in-part of Ser. No. 8,937, Jan. 30, 1987, Pat. No. 4,830,013.

[51] Int. Cl.⁵ .............................................. A61B 5/00
[52] U.S. Cl. .................................. 128/637; 128/632; 128/634; 128/692
[58] Field of Search ............... 128/665, 637, 912, 632, 128/634; 604/236, 230, 181, 27, 28, 154

[56] References Cited

U.S. PATENT DOCUMENTS

| Re. 31,879 | 5/1985 | Lubbers et al. | 436/133 |
|---|---|---|---|
| 2,629,399 | 2/1953 | Kulick | 604/118 |
| 3,433,935 | 3/1969 | Sherman | 128/634 |
| 3,461,856 | 4/1969 | Polanyi | 128/634 |
| 3,498,286 | 3/1970 | Polanyi et al. | 128/634 |
| 3,512,517 | 5/1970 | Kadish et al. | 128/634 |
| 3,529,591 | 9/1970 | Schuette | 128/632 |
| 3,612,866 | 10/1971 | Stevens | 128/634 |
| 3,616,409 | 10/1971 | Tosteson | 128/634 |
| 3,658,053 | 4/1972 | Fergusson et al. | 128/2 |
| 3,674,013 | 4/1972 | Polanyi | 128/634 |
| 3,807,390 | 4/1974 | Ostrowski et al. | 266/117 |
| 3,814,081 | 6/1974 | Mori | 356/41 |
| 3,841,308 | 10/1974 | Tate | 128/348 |
| 3,866,599 | 2/1975 | Johnson | 128/348 |
| 3,878,830 | 4/1975 | Bicher | 128/632 |
| 3,893,448 | 7/1975 | Brantigan | 128/348 |
| 3,983,864 | 10/1976 | Sielaff | 128/632 |
| 4,016,864 | 4/1977 | Sielaff | 128/632 |
| 4,050,450 | 9/1977 | Polanyi | 128/634 |
| 4,073,297 | 2/1978 | Kopp | 128/634 |
| 4,120,292 | 10/1978 | Le Blanc, Jr. et al. | 128/632 |
| 4,187,856 | 2/1980 | Hall et al. | 128/635 |
| 4,200,110 | 4/1980 | Peterson et al. | 128/634 |
| 4,201,222 | 5/1980 | Haase | 128/634 |
| 4,210,029 | 7/1980 | Porter | 73/705 |
| 4,265,249 | 5/1981 | Schindler | 128/635 |
| 4,274,417 | 6/1981 | Delpy | 128/632 |

(List continued on next page.)

FOREIGN PATENT DOCUMENTS 0273258 7/1988 European Pat. Off. .
1593270 7/1981 United Kingdom ............... 128/632

OTHER PUBLICATIONS

IEEE Transactions on Biomedical Engineering, vol. BME-33, No. 2, Feb. 1986, pp. 117-132, IEEE, New York; J. L. Gehrich et al.; "Optical Fluorescence and its Application to an Intravascular Blood Gas Monitoring System".

*Primary Examiner*—Francis Jaworski

U.S. PATENT DOCUMENTS

| | | | |
|---|---|---|---|
| 4,295,470 | 10/1981 | Shaw | 128/634 |
| 4,311,137 | 1/1982 | Gerard | 128/634 |
| 4,322,164 | 3/1982 | Shaw et al. | 128/632 |
| 4,360,615 | 7/1982 | Goodwin et al. | 128/635 |
| 4,398,542 | 8/1983 | Cunningham et al. | 128/675 |
| 4,407,290 | 10/1983 | Wilbur | 128/653 |
| 4,444,198 | 4/1984 | Petre | 128/673 |
| 4,471,765 | 9/1984 | Strauss et al. | 128/655 |
| 4,476,870 | 10/1984 | Peterson et al. | 128/634 |
| 4,476,877 | 10/1984 | Barker | 128/691 |
| 4,478,222 | 10/1984 | Koning et al. | 128/632 |
| 4,502,488 | 3/1985 | Degironimo et al. | 128/692 |
| 4,508,123 | 4/1985 | Wyatt et al. | 128/692 |
| 4,535,786 | 8/1985 | Kater | 128/760 |
| 4,543,961 | 10/1985 | Brown | 128/667 |
| 4,557,900 | 12/1985 | Heitzmann | 422/55 |
| 4,573,968 | 3/1986 | Parker | 604/67 |
| 4,585,007 | 4/1986 | Uchigaki et al. | 128/632 |
| 4,601,706 | 7/1986 | Aillon | 604/122 |
| 4,608,996 | 9/1986 | Brown et al. | 128/760 |
| 4,622,974 | 11/1986 | Coleman et al. | 128/634 |
| 4,640,820 | 2/1987 | Cooper | 422/68 |
| 4,651,741 | 3/1987 | Passafaro | 128/633 |
| 4,684,245 | 8/1987 | Goldring | 356/41 |
| 4,718,423 | 1/1988 | Willis et al. | 128/634 |
| 4,736,748 | 4/1988 | Nakamura et al. | 128/632 |
| 4,738,265 | 4/1988 | Ritchart et al. | 128/673 |
| 4,774,955 | 10/1988 | Jones | 128/632 |
| 4,785,814 | 11/1988 | Kane | 128/634 |
| 4,810,655 | 3/1989 | Khalil et al. | 128/634 |
| 4,830,013 | 5/1989 | Maxwell et al. | 128/637 |
| 4,841,974 | 6/1989 | Gumbrecht et al. | 128/635 |

*Assistant Examiner*—George Manue
*Attorney, Agent, or Firm*—Donald M. Sell; Walter N. Kirn; Dale E. Hulse

[57] ABSTRACT

A parameter of blood is sensed with a system which includes a catheter and a sensor and a volume oscillator element. The catheter has a lumen extending therethrough, a proximal end, a distal end and an opening, adapted to be placed in the blood vessel of a patient. The sensor senses a blood parameter and is adapted to be located outside the patient's body in fluid communication with the lumen. The volume oscillator element is in fluid communication with the lumen and is capable of acting to periodically cause blood to enter and exit the lumen. The system is structured so that a flush or anti-clotting solution flows into the patient when the volume oscillator element is inactive. With the volume oscillator activated, blood is moved back and forth in the lumen to expose the sensors to blood so that the blood parameter of interest can be sensed.

71 Claims, 3 Drawing Sheets

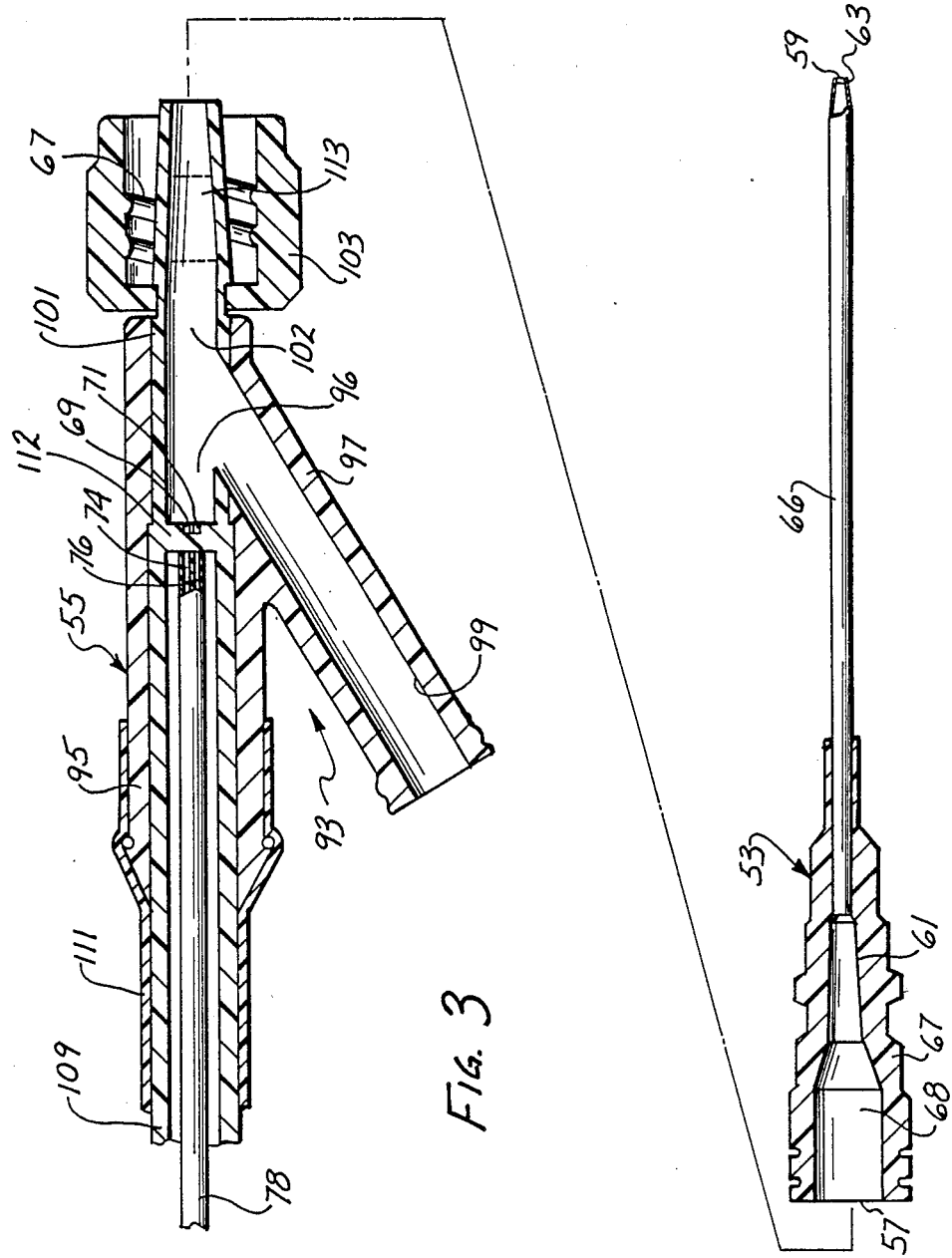

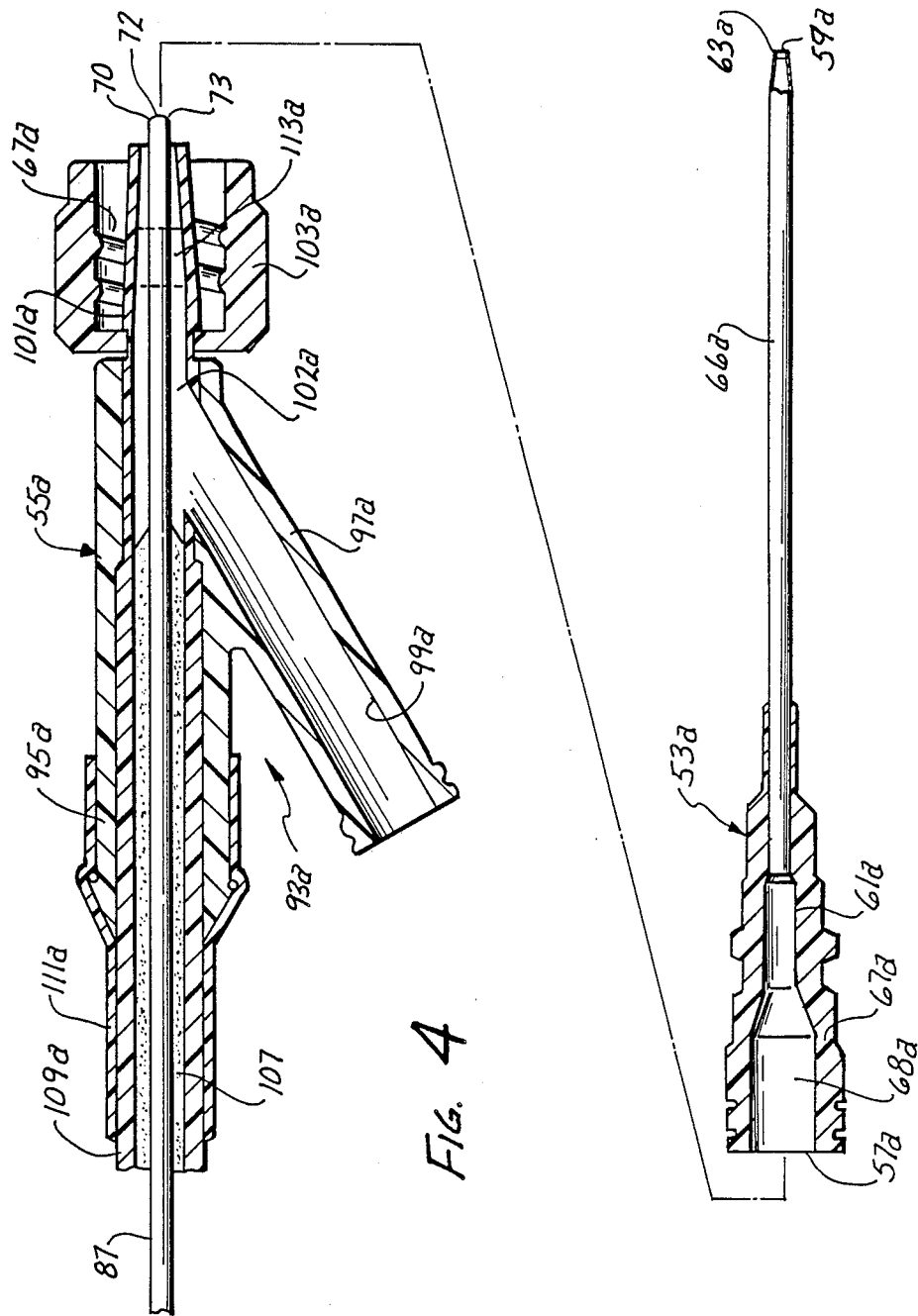

BLOOD PARAMETER MEASUREMENT SYSTEM

RELATED APPLICATION

This application is a continuation-in-part of co-pending application Ser. No. 008,937, filed Jan. 30, 1987 now U.S. Pat. No. 4,830,013.

BACKGROUND OF THE INVENTION

It is often necessary or desirable to measure various parameters of blood, such as temperature and blood constituents, such as blood gases, pH, other electrolytes and glucose. This can be accomplished in real time using fluorescent sensors. For example, this can be accomplished in an extracorporeal blood loop as shown in Cooper U.S. Pat. No. 4,640,820 and in vivo as disclosed in Lubbers et al Reissue Pat. No. 31,879. For in vivo sensing a probe or catheter carrying an appropriate sensor is inserted into a blood vessel of the patient. Because blood vessels are quite small, sensors designed to be inserted in such vessels must be very small. This size constraint may have a detrimental effect on the accuracy of the determination made by the sensor.

One of the most important gases that needs to be sensed is oxygen. One problem with in vivo oxygen sensing is that the readings obtained for the concentrations of oxygen tend to vary over an unacceptably wide range when compared with the results obtained using conventional laboratory techniques for measuring the concentration of oxygen. It has been found that this deviation is in many cases unacceptably large so that the reliability of the in vivo measuring system is called into question. Clearly, it would be advantageous to provide a system having many of the benefits of an in vivo measuring system while reducing or eliminating one or more of the deficiencies apparent in prior art in vivo systems.

Kater U.S. Pat. No. 4,535,786 discloses a method and apparatus for measuring parameters of body fluids, e.g., blood, using sensing electrodes which are calibrated periodically. Kater discloses a reversible pump, e.g., a two circuit positive displacement pump, to alternately pump calibration fluid, e.g., a modified and buffered ringer solution, from a source into contact with a reference electrode and, with the pump reversed, pump blood from the patient into contact with the sensing electrodes for taking measurements. In between measurements, the reversible pump is reversed again and operated at a reduced rate to pump a small amount of calibration fluid into the patient to keep the blood vessel open. Stopping the pump would stop the flow of calibration fluid. Kater discloses that all other infusions of liquid into the patient which come in contact with the electrodes are discontinued while blood is being drawn into contact with the electrodes. It would be advantageous to use sensors which did not require repeated calibration. Also, the use of a single reversible pump to pass calibration fluid into contact with a reference electrode at one flowrate, and into the patient at a different flowrate and to reverse and draw blood from the patient at a third flowrate, places an over-reliance on a single piece of equipment and/or requires relatively sophisticated equipment. A simpler system would be less costly and more reliable.

SUMMARY OF THE INVENTION

The present invention is based in part on the recognition and discovery that blood parameter sensors may not need to be exposed to pure blood in order to provide substantially accurate blood parameter measurements. Thus, it is not necessary that the flow of other fluids, e.g., anti-clotting and flush fluids, be interrupted while such measurements are being performed. Further, there is no need for stopping and starting fluid flows so that the equipment used is not taxed beyond its limits. Overall, the treatment of the patient is very effectively controlled, as desired.

In one broad aspect, the present invention involves an assembly which comprises a catheter, at least one sensor and a volume oscillator element. The catheter has a lumen extending through it, a proximal end, a distal end and a opening, preferably at or near the distal end. The catheter is sized and adapted so that at least the distal end and the opening are receivable within a blood vessel of a patient. The catheter acts to carry a fluid other than blood, e.g., an anti-clotting solution, from a fluid source to the patient. The sensor is for sensing the blood parameter and providing a signal in response thereto. The sensor is adapted to be located outside the patient's body, but in fluid communication with the lumen of the catheter. The volume oscillator element is in fluid communication with the lumen and is capable of acting to periodically cause blood to enter the lumen, be exposed to the sensor and exit the lumen. When the volume oscillator is inactive, i.e., when the volume oscillator is at rest, the flow of fluid from the fluid source to the patient is not stopped. Thus, unlike the reversible pump of Kater U.S. Pat. No. 4,535,786, which must be in operation, i.e., must be activated, in order for calibration fluid to flow, the present system provides for fluid, e.g., anti-clotting fluid, to flow into the patient even when the volume oscillator is inactive. In other words, fluids, such as anti-clotting fluids, can be provided to the patient without operating the volume oscillator. This substantially reduces the complexity of the present system while providing for reliable flow of fluids to the patient. Preferably, the volume oscillator element is structured and located so that substantially no net pumping of blood results from the operation of this element.

A further broad aspect of the invention involves an assembly comprising a catheter having a defined structure and at least one sensor. The catheter has a lumen extending therethrough, a proximal end, a distal end and an opening, preferably at or near the distal end. The distal end and the opening have cross-sectional areas sized to be receivable within the blood vessel of a patient. The lumen is structured so that blood from the patient moves in and out of the patient through the opening with substantially no net flow of blood. The sensor, e.g., as described above, is adapted to be located in a position in the lumen at or near the proximal end of the catheter. The cross-sectional area of the lumen nearest the position where the sensor is located is preferably larger than the cross-sectional area of the distal end or the above-noted opening of the catheter. The sensor or sensors are thus located in the catheter, but preferably at a less confined space relative to being located at or near the distal end of the catheter. Such sensor positioning can result in increased measurement accuracy and/or the use of physically bigger sensors.

An additional broad aspect of the invention involves an assembly comprising a probe and a catheter. The probe includes a sensor for sensing a parameter of blood and providing a signal in response thereto, an elongated transmission means for transmitting the signal from the sensor, and a fitting forming a primary fluid flow path, which preferably includes two non-aligned flow path segments which come together at a junction. In one embodiment, the sensor may be located in the fitting so as not to substantially protrude into the fluid flow path, thereby leaving this fluid flow path substantially unobstructed and reducing the risk of clot formation in the blood being sensed. The sensor may be located at or near the junction of the non-aligned flow path segments. The fitting preferably is a multi-legged fitting, more preferably a fitting having at least three legs and still more preferably a Y-fitting, having a first leg with which the elongated transmission means is associated, and a second leg and a third leg which together form the primary fluid flow path, preferably the only fluid flow path, through the fitting. The use of such multi-legged fittings, e.g., Y-fittings, is very convenient in this invention since such fittings are conventional and readily available. The sensor is preferably located in the fitting or in the catheter near the proximal end thereof. In one embodiment, the sensor is more preferably located in the first leg of a Y-fitting. The catheter, which is structured to be directly coupled to the fitting, has a lumen extending therethrough, a proximal end, a distal end and an opening, preferably adjacent the distal end. The catheter is sized and adapted so that at least the distal end and the opening thereof are receivable within a blood vessel of a patient.

In another broad aspect, the invention involves a method of sensing a parameter of blood. This method comprises providing a catheter in a blood vessel of a patient. This catheter has a lumen extending through it, a proximal end, a distal end and an opening at or near the distal end. A sensor, located outside the patient's body, is provided. This sensor is in fluid communication with the lumen and is capable of sensing a parameter of blood and providing a signal in response thereto. A flush solution from a flush solution source is introduced into the lumen so that there is an interface, e.g., interface zone, between the blood and the solution. A volume oscillator element, which is effective when active to at least aid in moving the interface back and forth in the lumen, is provided. The interface is moved back and forth in the lumen so that the sensor is exposed to blood for at least a portion of the time the interface is moving. The flow of flush solution from the flush solution source is not stopped when the volume oscillator element is inactive A signal, responsive to the blood parameter, is obtained from the sensor during the step of moving the interface. The present assembly can be used in practicing the present method.

Because the sensor is outside the body, it is effectively prevented from contacting the wall of the vessel. The sensor is not located so far back from the distal end of the catheter that it cannot perform its sensing function.

This invention recognizes that there is an interface between the blood and the flush solution. Theoretically, the interface could be a plane that simply divides the blood from the flush solution. However, in reality, the interface is a zone which has some axial length and which contains a mixture of the blood and the flush solution. Thus, the interface divides a zone of substantially all blood from a zone containing substantially all flush solution.

Because the flush solution is supplied to the catheter such that there is a net flow of solution through the opening at or near the distal end to the vessel, it would be expected that the interface would be entirely outside of, or at the distal end of, the catheter. However, by activating the present volume oscillator element to at least aid in moving the interface back and forth in the lumen, the sensor, even though it is located proximally from the distal end of the catheter, as described herein, can be exposed to blood for at least a portion of time that the interface is moving. This exposure must be sufficient to enable the sensor to provide an accurate signal related to the blood parameter of interest.

The movement of the interface back and forth in the lumen may move the interface over the sensor. However, the presently preferred fluorescent sensors, and in particular the fluorescent oxygen sensor, can tolerate some exposure to the mixture of flush solution and blood in the interface without providing erroneous readings. For example, it has been found that a mixture consisting of 50 percent blood by volume and 50 percent anti-clotting solution by volume yields approximately the same oxygen concentration as the oxygen concentration in a medium consisting essentially of blood.

Movement of the interface to bathe the sensor in blood is at least aided by the volume oscillator element, which is preferably located in the system for introducing the flush solution. The volume oscillator element may, for example, take the form of a syringe which, in effect, expands and contracts the volume of the introducing system to move the blood back and forth in the lumen. The volume oscillator may, and preferably does, include a solenoid operated plunger or piston and a flexible diaphragm. Movement of the piston causes the diaphragm to flex, thereby causing blood to move back and forth in the lumen, as desired. Preferably the movement of blood back and forth in the lumen is such that substantially no net pumping of blood results, e.g., from the operation of the volume oscillator. In other words, this back and forth movement of the interface creates no net or average flow of blood in either direction. This is substantially different from blood analysis performed in a conventional extracorporeal blood loop where blood is pumped from the patient's body to flow in one direction. As discussed above, the volume oscillator means is structured so that flush fluid, e.g., anti-clotting solution, continues to flow to the patient when this element is inactive.

Another technique, which is used in conjunction with the volume oscillator element, for aiding in moving the blood back and forth in the lumen, enables further expansion and contraction of the volume of the introducing system. This includes providing the introducing system with some compliance and allowing pressures generated by the patient's heartbeats to at least aid in moving the interface. Consequently, blood is forced to enter the opening at or near the distal end of the catheter as the blood pressure rises with each beat of the heart. Thus, the action of the volume oscillator element together with the patient's heartbeats act to cause the interface to flow back and forth in the lumen. In any event, the sensor is bathed by the back and forth or tidal movement of the blood and can adequately sense and measure the blood parameters of interest even though the sensor is located as described herein.

The compliance of the introducing system may be the natural compliance of the tubing and components of the system and/or a compliant element may be added to the system to provide the desired degree of elasticity. The compliant element can be of virtually any construction and may be, or include for example, a compressible fluid, such as air, a membrane (diaphragm), a bellows, etc. The compliance of the introducing system may be varied to obtain the results desired.

It may be necessary or desirable to take the patient's blood pressure through the lumen of the catheter while the blood parameters are being sensed. Just prior to taking a blood pressure reading, the action of the volume oscillator element is preferably stopped so that this element cannot affect the blood pressure reading taken through the lumen/catheter.

The sensor may be included as part of a probe. The probe may carry one or more sensors depending upon the number of parameters of interest. These sensors can be of any type, such as electro-chemical, that is suitable for sensing the parameter of interest. However, optical sensors are preferred, and fluorescent sensors are considered optimum. Although multiple sensors could be provided to sense the same blood parameter, preferably, each sensor senses a different blood parameter. In a preferred construction, the means acting to transmit the signal from the sensor includes an optical fiber for each of the sensors, with the sensor being located on the distal end of the associated optical fiber. The sensors provide signals related to the associated blood parameters of interest, and such signals may be used or processed continuously, intermittently or on demand to provide readings indicative of the blood parameters of interest.

The invention, together with additional features and advantages thereof, may best be understood by reference to the following description taken in connection with the accompanying illustrative drawings.

BRIEF DESCRIPTION OF THE DRAWINGS

FIG. 3 is a longitudinal sectional view through one embodiment of the probe-catheter assembly.

FIG. 4 is a longitudinal sectional view through another embodiment of the probe-catheter assembly.

DESCRIPTION OF THE PREFERRED EMBODIMENT

Figure 1:
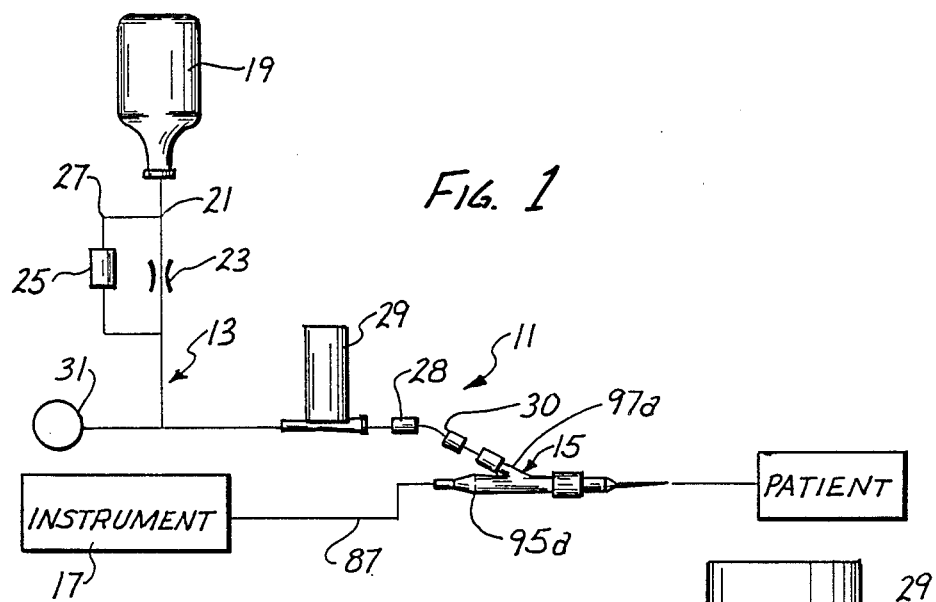
FIG. 1 is a schematic view of an assembly for the measurement of blood parameters of interest.

FIG. 1 shows an assembly 11 for the measurement of various blood parameters, and particularly the pH value and the concentrations of oxygen and carbon dioxide. Although the assembly 11 can be of different constructions, in this embodiment it includes a solution introducing system 13 and a probe-catheter assembly 15. The assembly 11 may also include an instrument 17 for providing a readout of the blood parameters of interest.

Generally, the solution introducing system 13 introduces an appropriate flush solution, e.g., an anti-clotting solution, such as a heparinized saline solution, through the probe-catheter assembly 15 to the patient to keep the line leading to the patient patent. Although this can be accomplished in different ways, in the embodiment shown schematically in FIG. 1, the system 13 includes a pressurized source 19 of heparinized saline solution, a conduit 21 leading from the source to the probe-catheter assembly 15, a flow restrictor 23 to reduce the rate of flow through the conduit 21 to the desired drop rate, a flush valve 25 in a bypass 27 around the restrictor 23, a stop cock 28, a volume oscillator 29, a blood withdrawal site 30 and a pressure transducer 31. Many of the components of the system 13 may be conventional, and the system 13 may include other components, if desired.

In the illustrated embodiment, solution from the pressurized source 19 flows through the restrictor 23 at a relatively slow rate, such as 5 ml/hour. The solution flows through the conduit 21, past the volume oscillator 29, through the probe-catheter assembly 15 to the patient. If a more rapid flow rate from the source 19 is desired, as for example during priming, the flush valve 25 can be manually opened to provide a relatively high-rate flow path around the restrictor 23 in a conventional manner.

Figure 2:
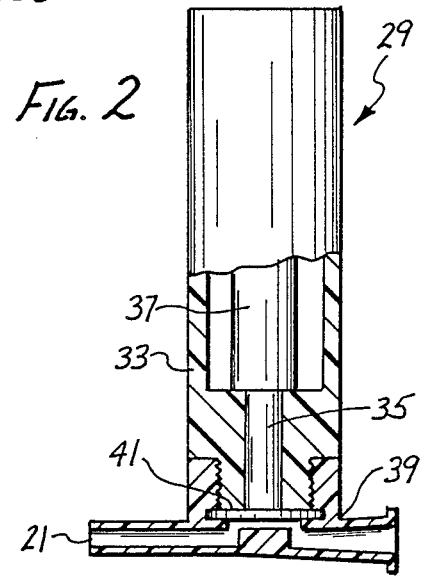
FIG. 2 is a close-up elevational view, partly in cross-section, of the volume oscillator in the assembly of FIG. 1.

FIG. 2 provides certain details of the volume oscillator 29. Although the volume oscillator 29 can take different forms, including that of a conventional syringe, in this embodiment it is illustrated schematically as including a cylinder 33, a plunger 35 slidable in the cylinder 33 and a linear solenoid 37 for reciprocating the plunger 35, as desired. A conduit segment 39 is threadedly attached to the bottom of the cylinder 33 and includes a flexible diaphragm 41. The conduit segment 39 provides part of the conduit 21 and also secures the volume oscillator 29 to the assembly 11. When the plunger 35 is moved upwardly, a chamber below the plunger 35 is created or enlarged causing the diaphragm 41 to flex upwardly in response to the resulting negative pressure above the diaphragm. This upward movement causes an expansion of the volume of the introducing system 13. Conversely, when the plunger 35 moves downwardly, the diaphragm flexes downwardly to thereby contract the volume of the introducing system 13. Expansion of the introducing system 13 pulls blood from the patient into probe-catheter assembly 15. Contraction of the introducing system 13 moves blood distally, with the amount of such movement being a function of the degree to which the volume oscillator 29 expands and contracts the volume of the introducing system 13. When the volume oscillator 29 is inactive, i.e., neither expanding nor contracting the volume of the introducing system 13, the flow of flush fluid from pressurized source 19 to the patient continues through the conduit 21.

The linear solenoid 37 can be operated continuously, intermittently or upon demand to create the desired blood movement, e.g., tidal action. Preferably the plunger 35 moves continuously so that the blood is never stationary in the probe-catheter assembly. There is no net or average flow or pumping of blood in either direction as a result of reciprocation of the plunger 35.

The pressure transducer 31 communicates with the conduit 21 and can measure the pressure therein. Accordingly, with the probe-catheter assembly 15 inserted into the vascular system of a patient, the pressure transducer 31 can provide blood pressure readings. By deactivating the volume oscillator 29, the position of the diaphragm is maintained in a neutral position and the volume oscillator 29 does not affect the blood pressure readings provided by the transducer 31. The blood withdrawal site 30 is used for taking blood samples from the patient through the probe-catheter assembly 15. The stop cock 28 is located between the volume oscillator 29 and the site 30 so that, by closing the stop cock 28, the anti-clotting solution in the system upstream of the stopcock 28 cannot be withdrawn during a blood withdrawal procedure.

As shown in FIG. 3, the probe catheter assembly 15 includes a catheter 53 and a probe 55. The catheter 53 may be a conventional arterial catheter. As such, the catheter 53 may include a proximal end 57, a lumen 61 extending axially, completely through the catheter 53 to a distal end 63 and an opening 59 at the distal end 63. The crosssectional area of the hollow space at proximal end 57 of catheter 53 is larger than the cross-sectional area of the hollow space at distal end 63 of catheter 53. The catheter 53 has an externally threaded coupling 67 at its proximal end 57 with a relatively large diameter portion 68 of the lumen and an elongated catheter body 66 sized to be received in a vein or artery and having a much smaller diameter portion of the lumen extending axially therethrough.

The probe may be of various different constructions. In the embodiment illustrated in FIG. 3, the probe 55 includes an oxygen sensor 69, and a carbon dioxide sensor 71 located proximally to the proximal end 57 of catheter 53. The cross-sectional area of the hollow space in which sensors 69 and 71 are located is larger than the cross sectional area of the lumen at the distal end 63 of catheter 53. Sensors 69 and 71 are associated with the distal ends of optical fibers 74 and 76, respectively, both of which are included in a bundle sheath 78. The construction and operation of sensors 69 and 71 are more fully described in Heitzmann U.S. Pat. No. 4,557,900, which is incorporated in its entirety by reference herein.

Probe 55 includes a "Y" fitting 93 as shown in FIG. 3. Optical fibers 74 and 76 extend within the bundle sheath 78 completely through one leg 95 of the "Y" fitting 93 to instrument 17 as shown in FIG. 1. The sensors 69 and 71 are exposed in a relatively large diameter passage 96 in the leg 95 and therefore may be larger than if they were in the relatively small diameter portion of the lumen 61. One or more other sensors, not shown, may be included with sensors 69 and 71. Of course the sensors 69 and 71 could be positioned elsewhere such as in the large diameter portion of the lumen 68. In either event the cost associated with miniaturization is reduced or eliminated. Also, with the sensors 69 and 71 located in the leg 95, they do not impede fluid flow. Another leg 97 of "Y" fitting 93 has a passage 99 which communicates with the lumen 61. Leg 97 is coupled to the conduit 21 of system 13 as shown in FIG. 1. A third leg 101 of "Y" fitting 93 has a passage 102 and carries a rotatable internally threaded coupling 103 for attaching the "Y" fitting of probe 55 to the proximal end 57 of catheter 53 outside the cardiovascular system of the patient. Passages 99 and 102 together form the fluid flow-path through "Y" fitting 93.

Bundle sheath 78 extends within a flexible tube 109 suitably attached to the leg 95, and shrink tubing 111 is provided over the adjacent end portion of fitting 93 and tube 109 for strain relief. The sensors 69 and 71 are carried by an end wall 112 of the tube 109 and the end wall is transparent to light at the excitation and fluorescent emission wavelengths for the sensors.

With the proximal end 57 of catheter 53 coupled to probe 55 by coupling 103, sensors 69 and 71 of probe 55 are in communication with lumen 61. Accordingly, with catheter 53 within the cardiovascular system of the patient, such as in a radial artery, the sensors 69 and 71 are kept from contacting the wall of the artery to thereby substantially eliminate any wall effect and any clot effect on the signals provided by the sensors 69 and 71.

In use of assembly 11, catheter 53 is first inserted into the radial artery using conventional techniques. Probe 55 is attached to the proximal end 57 of catheter 53 with coupling 103. This properly positions sensors 69 and 71 relative to lumen 61.

When in use, the anti-clotting solution from source 19 completely fills the space around the portion of probe 55 in the lumen 61. The solution is provided under a pressure such that there is a slow flow of solution from lumen 61 into the patient's artery. This introduction of the solution into the catheter 53 results in an interface 113 which has some axial length and which includes both blood and the solution from source 19. The interface 113 is a partition between essentially all blood distally of the interface 113 and essentially all anti-clotting solution proximally of the interface 113. The interface 113 is shown in the passage 102 in FIG.3, but it washes axially back and forth in a tidal action as a result of the rising and falling of the patient's blood pressure with each heartbeat and the action of volume oscillator 29. If the solution introducing system 13 were perfectly rigid, it would not be possible for the blood to force the anti-clotting solution proximally within the lumen 61 because the solution is essentially incompressible. However, the solution introducing system 13, including the conduit 21, is typically in the form of flexible plastic tubing which has some elasticity or compliance to allow this tidal action to occur.

With this embodiment of the invention, the back and forth travel of the interface 113 is a function of the magnitude of the patient's blood pressure, the compliance of solution-introducing system 13, the action of volume oscillator 29 and the delivery pressure of the anti-clotting solution. However, the interface should move proximally at least to the sensors 69 and 71 and preferably into the passage 99 sufficiently to bathe the sensors in essentially all blood. Also, since there is some net flow of the anticlotting solution out of catheter 53, it would be necessary for at least the distal region of interface 113 to travel distally as far as the opening, e.g., the distal opening 59, of catheter 53 unless it is possible for some of the solution to migrate through the blood and through the opening or openings of catheter 53. The precise manner in which the solution enters the patient's bloodstream and the exact extent of travel of the interface is not known. However, utilizing the tidal action of the interface, it is possible to bathe the sensors 69 and 71 in blood sufficiently so that accurate readings are obtained, and it is believed that the sensors are in essentially all blood for at least a portion of the time.

Figure 6:
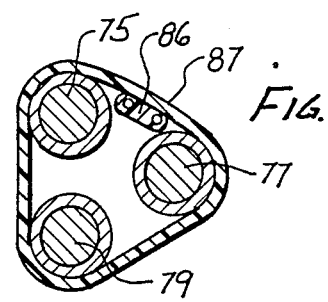
FIG. 6 is an enlarged sectional view taken generally along line 6—6 of FIG. 5.
Figure 5:
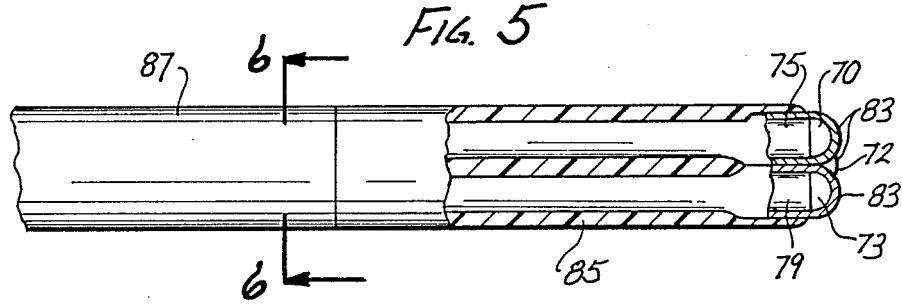
FIG. 5 is an enlarged fragmentary sectional view of the distal region of one form of probe usable in the assembly of FIG. 1.

FIGS. 4, 5 and 6 show another embodiment of this invention which is identical to the embodiment of FIGS. 1, 2 and 3 in all respects not shown or described herein. Portions of the embodiment of FIGS. 4, 5 and 6 substantially identical to portions of the embodiment of FIGS. 1, 2 and 3 are designated by corresponding reference numerals followed by the letter "a".

As illustrated in FIGS. 4 and 5, the probe 55a includes an oxygen sensor 70, a carbon dioxide sensor 72 and a pH sensor 73, affixed to the distal ends of single optical fibers 75, 77 and 79, respectively. In this embodiment, sensors 70, 72 and 73 are fluorescent optical sensors, and they respond to the concentration of oxygen, the concentration of carbon dioxide and the pH, respectively, in the patient's blood to provide continuous optical signals indicative of the condition sensed. Optical fibers 75, 77 and 79 serve as transmission means for transmitting the signals from the associated sensors proximally.

Sensors 70, 72 and 73 are attached to the distal ends of associated optical fibers 75, 77 and 79 in any suitable manner, and each sensor and its associated fiber is separately encased in an inner overcoat 83 which, among other things, may assist in retaining the sensor on the end of the associated fiber. The overcoat 83 is permeable to the relevant blood parameter of interest so that such parameter, or one related to it, can be sensed by the sensor. An outer overcoat 85 covers the inner overcoats 83 and a length of the fibers just proximally of the inner overcoats 83. Proximally of the overcoat 85, the optical fibers 75, 77 and 79 and a temperature-sensitive element, such as a thermocouple 86 (FIG. 6), are suitably encased within an appropriate sheath 87.

Probe 55a includes a "Y" fitting 93a as shown in FIG. 4. Optical fibers 75, 77 and 79 extend within the sheath 87 completely through one leg 95a of the "Y" fitting 93a to instrument 17. Sheath 87, with sensors 70, 72 and 73, extends through passage 102a of third leg 101a and is positioned with its distal end just inside relatively large diameter portion 68a of lumen 61a, inside coupling 67a. Sheath 87 is retained in position by potting 107. Another leg 97a of "Y" fitting 93a has a passage 99a which communicates with the lumen 61a. Passages 99a and 102a together from the fluid flow passage through "Y" fitting 93a. Leg 97a is coupled to the conduit 21 of system 13. Third leg 101a of "Y" fitting 93a carries a rotatable internally threaded coupling 103a for attaching the "Y" fitting 93a of probe 55a to the proximal end 57a of catheter 53a outside the cardiovascular system of the patient.

Sheath 87 extends within a flexible tube 109a suitably attached to the leg 95a, and shrink tubing 111a is provided over the adjacent end portion of fitting 93a and tube 109a for strain relief.

The primary difference between the embodiments of FIGS. 3 and 4–6 is in the mounting and positioning of the sensors. Thus, in the embodiment of FIGS. 4–6, the sensors 70, 72 and 73 are in the lumen portion 68a of the catheter 53a, while the sensors 69 and 71 of the embodiment of FIG. 3 are located proximally of catheter 53.

In use, the embodiment shown in FIGS. 4, 5 and 6 operates and functions in much the same manner as the embodiment of FIG. 3. Of course, the position of sheath 87 can be varied axially with respect to fitting 93a, as desired, to provide that sensors 70, 72 and 73 are sufficiently exposed to blood so as to provide satisfactory determinations of the blood parameters of interest.

Although exemplary embodiments of the invention have been shown or described, many changes, modifications and substitutions may be made by one having ordinary skill in the art without necessarily departing from the spirit and scope of this invention.

What is claimed is:

1. An assembly for the sensing of a blood parameter comprising:
    a catheter having a proximal end, a distal end, and a lumen extending therethrough, said lumen having an opening in said distal end, said catheter being sized and adapted so that at least said distal end and said opening are receivable within a blood vessel of a patient, said catheter acting to carry a fluid other than blood from a fluid source, through said lumen and opening, and into said patient;
    sensor means, in fluid communication with said lumen, for sensing said blood parameter and providing a signal in response thereto;
    a multi-legged fitting coupled to said catheter, said multi-legged fitting having two legs which form the only primary fluid flow path through said multi-legged fitting, said sensor means being located in said multi-legged fitting; and
    a volume oscillator element in fluid communication with said lumen and being capable of acting to periodically cause blood to enter said lumen and to exit said lumen as desired, said volume oscillator element not interfering with the flow of said fluid through said lumen and opening when said volume oscillator element is inactive.

2. The assembly of claim 1 wherein said volume oscillator element is structured and located so that the operation of said volume oscillator element does not affect the net flow of blood in either direction through said lumen.

3. The assembly of claim 1 which further comprises a conduit for coupling said lumen to said source of fluid whereby said fluid can be supplied to said lumen.

4. The assembly of claim 3 wherein said volume oscillator element is in fluid communication with said conduit.

5. The assembly of claim 1 wherein said sensor means is an optical sensor.

6. The assembly of claim 1 wherein said sensor means is a fluorescence sensor.

7. The assembly of claim 1 which further comprises transmission means for transmitting said signal from said sensor means.

8. The assembly of claim 7 wherein said transmission means comprises an optical fiber.

9. The assembly of claim 1 which further comprises one or more additional sensor means, each of said sensor means sensing a different blood parameter.

10. The assembly of claim 9 which further comprises a plurality of elongated transmission means, each of which is associated with a different one of said sensor means.

11. The assembly of claim 10 wherein each of said sensor means is located at or near a distal end of its associated elongated transmission means.

12. The assembly of claim 10 wherein the number of said sensor means equal sat least three.

13. The assembly of claim 1 wherein said volume oscillator element comprises a piston movable in a chamber to increase or decrease an open volume of said chamber as desired, and a diaphragm movable in response to the increasing or decreasing of said open volume.

14. The assembly of claim 13 wherein said piston is capable of reciprocating in said chamber to increase or decrease the open volume of said chamber as desired.

15. The assembly of claim 14 wherein said piston is motor driven.

16. The assembly of claim 1 wherein said blood parameter is selected from the group consisting of blood gases, pH electrolytes, and glucose.

17. An assembly for the sensing of a blood parameter comprising:
    a catheter having a proximal end, a distal end, and a lumen extending therethrough, said lumen having an opening in said distal end, said distal end having a cross-sectional area of such size that said distal end and said opening are receivable within a blood vessel of a patient;

sensor means for sensing said blood parameter and providing a signal in response thereto, said sensor means being located at a position in said lumen of said catheter at or near the proximal end of said catheter; and a volume oscillator element in fluid communication with said lumen and being capable of acting to periodically cause blood to enter said lumen and to exit said lumen, wherein the operation of said volume oscillator element does not affect the net flow of blood in either direction through said lumen.

18. The assembly of claim 17 wherein the cross-sectional area of said lumen at the position of said sensor means is greater than the cross-sectional of said distal end or of said opening.

19. The assembly of claim 18 wherein said volume oscillator element comprises a piston movable in a chamber to increase or decrease an open volume of said chamber as desired, and a diaphragm movable in response to the increasing or decreasing of said open volume.

20. The assembly of claim 19 wherein said piston is capable of reciprocating in said chamber to increase or decrease the open volume of said chamber as desired.

21. The assembly of claim 20 wherein said piston is motor driven.

22. The assembly of claim 17 wherein said sensor means is an optical sensor.

23. The assembly of claim 17 wherein said sensor means is a fluorescence sensor.

24. The assembly of claim 17 which further comprises transmission means for transmitting said signal from said sensor means.

25. The assembly of claim 24 wherein said transmission means comprises an optical fiber.

26. The assembly of claim 17 which further comprises one or more additional sensor means, each of said sensor means sensing a different blood parameter.

27. The assembly of claim 26 which further comprises a plurality of elongated transmission means, each of which is associated with a different one of said sensor means.

28. The assembly of claim 27 wherein each of said sensor means is located at or near a distal end of its associated elongated transmission means.

29. The assembly of claim 27 wherein the number of said sensor means equals at least three.

30. The assembly of claim 17 wherein said blood parameter is selected from the group consisting of blood gases, pH, electrolytes, and glucose.

31. The assembly of claim 1 wherein said multi-legged fitting has a first leg, a second leg, and a third leg, said second and third legs forming said primary fluid flow path through said multi-legged fitting.

32. The assembly of claim 31 wherein said sensor means is located in said first leg.

33. The assembly of claim 31 wherein said sensor means comprises an optical sensor and wherein an optical fiber is associated with said first leg, said optical fiber serving to receive said signal from said optical sensor.

34. The assembly of claim 33 wherein said optical fiber also serves to deliver excitation light to said optical sensor.

35. A probe-catheter assembly comprising:

a probe including sensor means for sensing a parameter of blood and providing a signal in response thereto, elongated transmission means for transmitting said signal from said sensor means, and a multi-legged fitting having a first leg with which said elongated transmission means is associated, and a second leg and a third leg which together form the only primary fluid flow path through said multi-legged fitting; and a catheter having a proximal end, a distal end, and a lumen extending therethrough, said lumen having an opening in said distal end, said catheter being sized and adapted so that at least said distal end and said opening are receivable within a blood vessel of a patient, said catheter being structured to be coupled to said multi-legged fitting, said sensor means being located in said multi-legged fitting or in said catheter near the proximal end thereof.

36. The probe-catheter assembly of claim 35 wherein said sensor means is located in said first leg.

37. The probe-catheter assembly of claim 36 wherein said first leg at said location of said sensor means has a larger cross-sectional area than the cross-sectional area of said lumen at said distal end.

38. The probe-catheter assembly of claim 35 wherein said sensor means is located in said catheter near the proximal end thereof.

39. The probe-catheter assembly of claim 35 wherein said multi-legged fitting is a Y-fitting.

40. The probe-catheter assembly of claim 35 which further comprises a first coupling component forming part of said catheter and a second coupling component for coupling said catheter to said multi-legged fitting.

41. The probe-catheter assembly of claim 40 wherein said lumen extends through said first coupling component, the cross-sectional area of said lumen within said first coupling component being greater than the cross-sectional area of said lumen at said distal end.

42. The probe-catheter assembly of claim 35 wherein said sensor means is positioned so as to not substantially protrude into said primary fluid flow path.

43. A probe-catheter assembly comprising:

a probe including sensor means for sensing a parameter of blood and providing a signal in response thereto, elongated transmission means for transmitting said signal from said sensor means, and a fitting including two non-aligned flow path segments which come together at a junction, said two non-aligned flow path segments forming the only primary fluid flow path through said fitting; and a catheter having a proximal end, a distal end, and a lumen extending therethrough, said lumen having an opening in said distal end, said catheter being sized and adapted so that at least said distal end and said opening are receivable within a blood vessel of a patient, said catheter being coupled to said fitting, said sensor means being located in said fitting at or near said junction.

44. The probe-catheter assembly of claim 43 wherein said sensor means is positioned so as to not substantially protrude into said primary fluid flow path.

45. The probe-catheter assembly of claim 35 wherein said sensor means comprises an optical sensor and said elongated transmission means comprises an optical fiber.

46. The probe-catheter assembly of claim 45 wherein said optical sensor is a fluorescence sensor.

47. A method of sensing a parameter of blood comprising:
provided a catheter having a proximal end, a distal end, and a lumen extending therethrough, said lumen having an opening in said distal end, at least said opening of said catheter being positioned within a blood vessel of a patient;
providing sensor means outside the body of said patient in fluid communication with said lumen, said sensor means being capable of sensing a parameter in blood and providing a signal in response thereto;
introducing a flush solution from a flush solution source into said lumen so that there is an interface between blood from the patient and said solution;
providing a volume oscillator element which, when activated, aids in moving said interface back and forth so that said sensor means is exposed to blood for at least a portion of the time that said interface is moving, and continuing the flow of said flush solution from said flush solution source into said lumen when said volume oscillator element is inactive; and
obtaining said signal from said sensor means during the time said sensor is exposed to blood.

48. The method of claim 47 which further comprises allowing said patient's heart contractions to partially move said interface.

49. The method of claim 47 wherein said interface is moved back and forth over said sensor means.

50. The method of claim 47 wherein said introducing step includes introducing said flush solution into said lumen to produce a net flow of said solution through said opening and into said blood vessel of said patient.

51. The method of claim 47 which further comprises deactivating said volume oscillator element for a desired time period, and taking a blood pressure reading while said volume oscillator element is inactive.

52. The method of claim 47 wherein the action of said volume oscillator element does not affect the net flow of blood in either direction through said lumen.

53. The method of claim 47 further comprising the step of continuing the flow of said flush solution from said flush solution source into said lumen when said volume oscillator element is active or inactive.

54. A method of sensing a parameter of blood comprising:
providing a catheter having a proximal end, a distal end, and a lumen extending therethrough, said lumen having an opening in said distal end, at least said opening of said catheter being positioned within a blood vessel of a patient;
providing sensor means outside the body of said patient in fluid communication with said lumen, said sensor means being capable of sensing a parameter of blood and providing a signal in response thereto;
introducing an anti-clotting solution into said lumen from an anti-clogging solution source through a variable volume solution-introducing system so that there is a net flow of said anti-clogging solution through said opening into said blood vessel of said patient; and
providing a volume oscillator element in fluid communication with said solution-introducing system which volume oscillator element, when activated, aids in moving blood from said blood vessel through said opening and into said lumen so as to expose said sensor means to blood and obtain a signal in response to said parameter of said blood, and continuing the flow of said anti-clotting solution from said anti-clotting solution source into said lumen when said volume oscillator element is active or inactive.

55. The method of claim 54 which further comprises allowing the pressure generated by the patient's heart contractions to partially move said blood back and forth in said lumen.

56. The method of claim 54 wherein the action of the volume oscillator element does not affect the net flow of blood in either direction through said lumen.

57. The method of claim 54 which further comprises deactivating said volume oscillator element for a desired period of time, and taking a blood pressure reading while said volume oscillator element is inactive.

58. An assembly for the sensing of a blood parameter comprising:
a catheter having a proximal end, a distal end, and a lumen extending therethrough, said lumen having an opening in said distal end, said catheter being sized and adapted so that at least said distal end and said opening are receivable within a blood vessel of a patient, said catheter acting to carry a fluid other than blood from a fluid source, through said lumen and opening, and into said patient;
sensor means, in fluid communication with said lumen, for sensing said blood parameter and providing a signal in response thereto, said sensor means being located in said catheter near the proximal end thereof; and
a volume oscillator element in fluid communication with said lumen and being capable of acting to periodically cause blood to enter said lumen and to exit said lumen as desired, said volume oscillator element not interfering with the flow of said fluid through said lumen and opening when said volume oscillator element is inactive.

59. The assembly of claim 58 wherein said sensor means is an optical sensor.

60. The assembly of claim 58 wherein said sensor means is a fluorescence sensor.

61. The assembly of claim 58 wherein said blood parameter is selected from the group consisting of blood gases, pH, electrolytes, and glucose.

62. The assembly of claim 58 further comprising a multi-legged fitting coupled to said catheter, said multi-legged fitting having a first leg, a second leg, and a third leg, said second and third legs forming the only primary fluid flow path through said multi-legged fitting.

63. The assembly of claim 62 wherein said sensor means comprises an optical sensor and wherein an optical fiber is associated with said first leg, said optical fiber serving to receive said signal from said optical sensor.

64. An assembly for the sensing of a blood parameter comprising:
a catheter having a proximal end, a distal end, and a lumen extending therethrough, said lumen having an opening in said distal end, said catheter being sized and adapted so that at least said distal end and said opening are receivable within a blood vessel of a patient, said catheter acting to carry a fluid other than blood from a fluid source, through said lumen and opening, and into said patient;
sensor means for sensing said blood parameter and providing a signal in response thereto, said sensor means being adapted to be located outside the body of said patient in fluid communication with said lumen; and a volume oscillator element in fluid communication with said lumen and being capable of acting to periodically cause blood to enter said lumen and to exit said lumen as desired, said assembly allowing the flow of said fluid into said lumen when said volume oscillator element is active or inactive.

65. The assembly of claim 64 wherein said sensor means is an optical sensor.

66. The assembly of claim 64 wherein said sensor means is a fluorescence sensor.

67. The assembly of claim 64 wherein said blood parameter is selected from the group consisting of blood gases, pH, electrolytes, and glucose.

68. The assembly of claim 64 further comprising a multi-legged fitting coupled to said catheter, said multi-legged fitting having a first leg, a second leg, and a third leg, said second and third legs forming the only primary fluid flow path through said multi-legged fitting.

69. The assembly of claim 68 wherein said sensor means is located in said first leg.

70. The assembly of claim 68 wherein said sensor means comprises an optical sensor and wherein an optical fiber is associated with said first leg, said optical fiber serving to receive said signal from said optical sensor.

71. The assembly of claim 64 wherein said sensor means is located in said catheter near the proximal end thereof.

* * * * *

UNITED STATES PATENT AND TRADEMARK OFFICE
CERTIFICATE OF CORRECTION

PATENT NO.   : 4,951,669
DATED        : August 28, 1990
INVENTOR(S)  : Thomas P. Maxwell et al.

It is certified that error appears in the above-identified patent and that said Letters Patent is hereby corrected as shown below:

Col. 9, line 29, "from" should be --form--.

Col. 10, line 48, "equal sat" should be --equals at--.

Col. 10, line 62, "pH electrolytes" should be --pH, electrolytes--.

Col. 11, line 16, after "cross-sectional" insert --area--.

Col. 13, line 57, "anti-clogging" should be --anti-clotting--.

Col. 13, line 59, "anti-clogging" should be --anti-clotting--.

Signed and Sealed this

Twenty-eighth Day of April, 1992

Attest:

HARRY F. MANBECK, JR.

*Attesting Officer*   *Commissioner of Patents and Trademarks*